United States Patent [19]
Gogolewski et al.

[11] Patent Number: 5,728,336
[45] Date of Patent: Mar. 17, 1998

[54] HIGH-STRENGTH, HIGH-MODULUS, COMPOUND-FILAMENT OR COMPOUND-FILM IMPLANT AND METHOD FOR PRODUCING IT

[75] Inventors: Sylwester Gogolewski, Alvaneu-Dorf; Slobodan Tepic, Davos, both of Switzerland

[73] Assignee: Synthes (U.S.A.), Paoli, Pa.

[21] Appl. No.: 426,684

[22] Filed: Apr. 14, 1995

Related U.S. Application Data

[63] Continuation of Ser. No. 658,552, Feb. 21, 1991, abandoned.

[51] Int. Cl.⁶ .................................................. B29C 65/70
[52] U.S. Cl. ............................ 264/101; 156/180; 264/83; 264/331.17; 264/343; 623/18; 623/16
[58] Field of Search ........................ 264/343, 289.6, 264/210.3, 49, 331, 17, 205, 101, 83; 156/180; 623/18, 16

[56] References Cited

U.S. PATENT DOCUMENTS

| | | | |
|---|---|---|---|
| 2,271,192 | 1/1942 | Hinz | 264/343 |
| 3,549,789 | 12/1970 | Haroldson | 264/343 |
| 3,777,002 | 12/1973 | Suzuki et al. | 264/343 |
| 3,839,516 | 10/1974 | Williams et al. | 264/41 |
| 4,587,163 | 5/1986 | Zachariades | 264/331.17 |
| 4,662,887 | 5/1987 | Turner et al. | 623/16 |
| 4,880,002 | 11/1989 | MacGregor | 128/339 |
| 4,883,618 | 11/1989 | Barrows | 264/343 |
| 4,902,297 | 2/1990 | Devanathan | 623/16 |
| 5,026,511 | 6/1991 | Sano et al. | 264/331.17 |
| 5,342,395 | 8/1994 | Jarrett et al. | 606/219 |

*Primary Examiner*—Jeffery R. Thurlow
*Attorney, Agent, or Firm*—McAulay Fisher Nissen Goldberg & Kiel, LLP

[57] ABSTRACT

High-strength, high-modulus, polymeric implants are produced from highly oriented monofilaments and/or films by solvent welding technique. This avoids loss of orientation, as well as thermal and oxidative degradation, which is the common case with the state of art techniques, namely melt extrusion, injection molding and heat compression molding. The invention leads to uniform bonding of the separate structural units (monofilaments or films) into compound-filament or compound-laminate which protects the implant against delamination. Monofilaments of films are swollen at the surface with a suitable solvent which does not destroy the orientation in the core. A bundle, resp. a sandwich of the swollen monofilaments or films is pulled through an orifice generating compressive stresses between the filaments, resp. films. Solvent removal from the swollen compressed interfaces leads to a homogenous welding of the monofilaments or films.

8 Claims, 6 Drawing Sheets

HIGH-STRENGTH, HIGH-MODULUS, COMPOUND-FILAMENT OR COMPOUND-FILM IMPLANT AND METHOD FOR PRODUCING IT

This is a continuation of application Ser. No. 07/658,552, filed Feb. 21, 1991, now abandoned.

BACKGROUND OF THE INVENTION

This invention relates to a high-strength, high-modulus, polymeric implant materials comprising a plurality of polymeric structural units with highly oriented cores embedded in an unoriented polymeric matrix and a method for producing it.

Use of polymeric materials for surgical implants requires high strength currently attainable only by fibre or film production technologies, i.e. melt extrusion or solution spinning, followed by hot drawing. These fibres can be used to reinforce materials to produce strong composites. When composite materials are used to produce implants, the aggressive in vivo environment exacerbates the problems of delamination. When the heat is used to produce monofilament reinforced composites, extensive thermal and oxidative degradation of the polymer lead to premature loss of mechanical properties and chemical stability in vivo.

SUMMARY OF THE INVENTION

The invention as claimed is intended to remedy these drawbacks.

It is an object of this invention to provide a high-strength, high-modulus, compound-filament or film-laminate, polymeric implant material resistant to delamination and a method for producing it.

Preferably the implant material is chemically homogeneous but it is also possible to use chemically different materials compatible with each other. Preferred implant materials to be used in the invention are thermoplastic polymers, in particular polyethylenes, polyethylene terephthalates, polycaproamides and polylactides. Molecular weight of these polymeric materials and molecular weight distribution should be chosen to meet the requirements for fiber-forming and/or film-forming using any of the suitable methods known to those skilled in-the-art.

The basic steps of the method for producing the implant material according to the invention are:

1) Surface swelling of the oriented polymeric structural units (monofilaments or films) in a suitable solvent. Suitable solvents are those which dissolve a particular polymer, but which at the same time are easily removable from the polymeric material.

2) Forming a monofilament bundle or a film sandwich and pulling it through an orifice (or passing them between rollers) where the area of the orifice at its narrowest point is equal to or smaller than the total cross-sectional area of the monofilaments in the bundle or the films in the sandwich.

3) Maintaining tension on the compound-filament, resp. of the film laminate past the orifice and removing the solvent.

The various features of novelty which characterize the invention are pointed out with particularity in the claims annexed to and forming part of this disclosure. For the better understanding of the invention, its operating advantages and specific objects attained by its use, reference should be had to the accompanying drawings and descriptive matter in which are illustrated and described preferred embodiments of the invention.

DESCRIPTION OF THE PREFERRED EMBODIMENTS

FIG. 1 illustrates the geometrical requirements on the process of compound-filament formation.

Figure 1A:
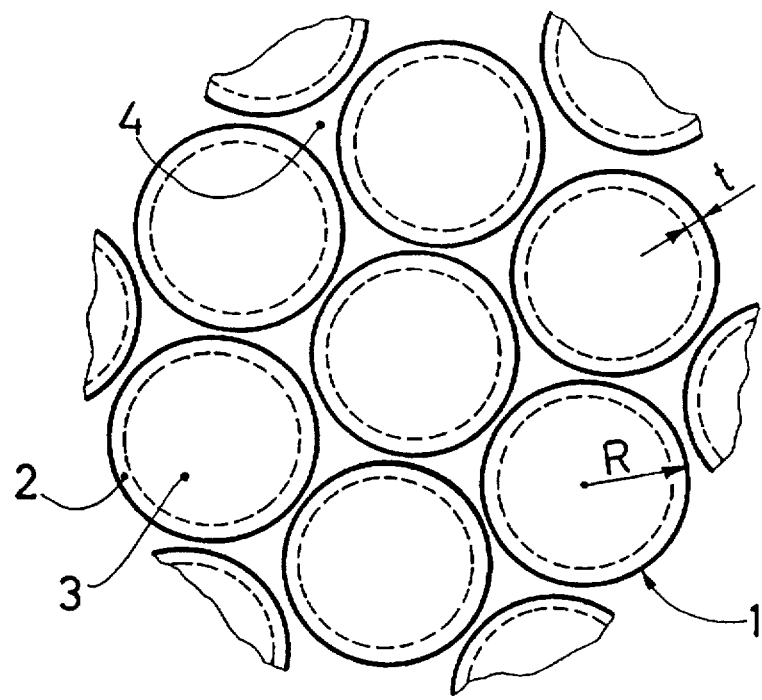
FIGS. 1(a) and 1(b) are partial sections through a bundle of monofilaments of the implant materials according to the invention showing the geometrical parameters.

In FIG. 1a monofilaments 1 of circular cross sections with the radius R are aligned in a bundle. Surface swelling of the monofilaments 1 by a solvent creates a skin 2 of highly viscous solution. A gradient of solvent concentration is established by diffusion, still leaving an intact highly oriented core 3 of the monofilaments 1. The filaments 1 are tightly packed in a bundle leaving voids 4.

Figure 1B:
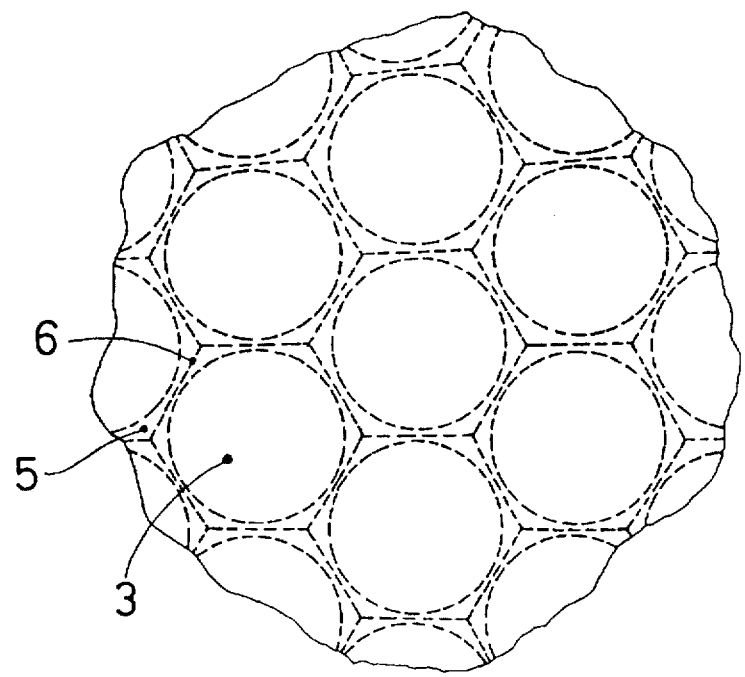
Figure 2:
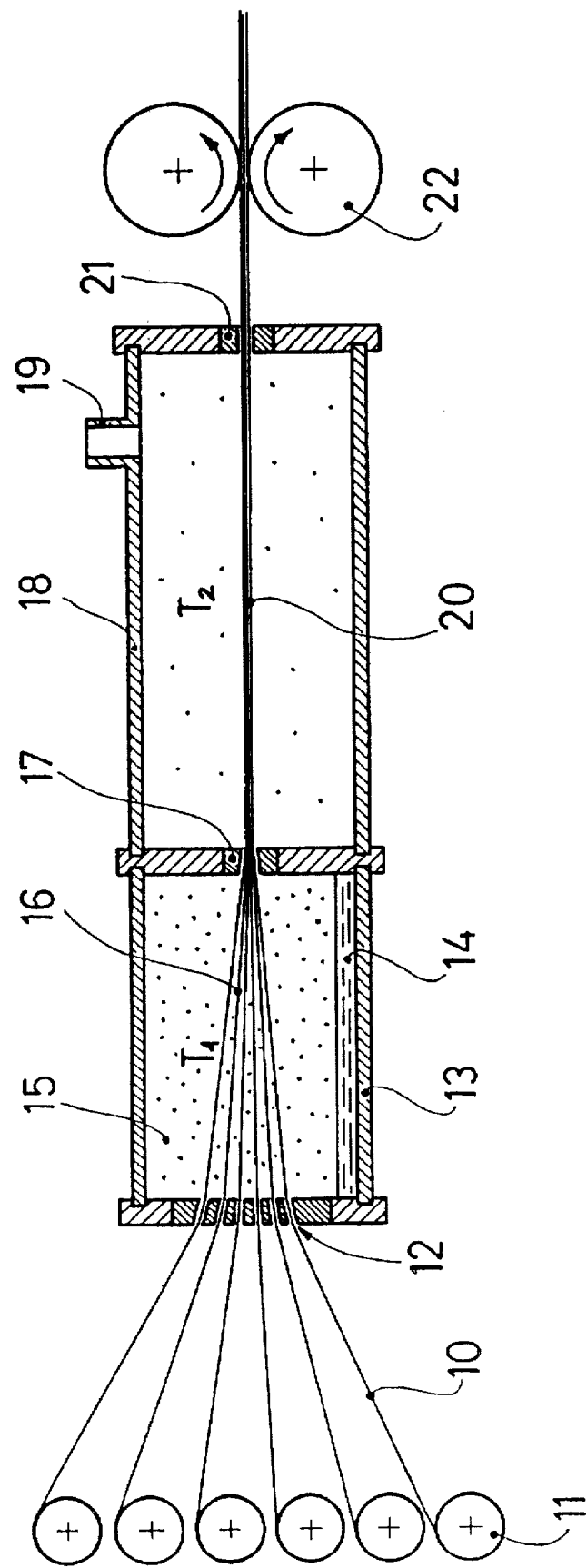
FIG. 2 is a schematic sectional view of the processing equipment for production of the compound-filaments of the implant materials according to the invention.

FIG. 1b shows a compressed bundle of monofilaments 1 (as obtained after passing the exit of the orifice of the processing equipment represented in FIG. 2). Highly viscous, swollen skins 5 (skin 2 of FIG. 1(a) have been deformed, eliminating the voids 4 of FIG. 1a and joined along the planes 6. Solvent removal is affected mostly by diffusion through these regions of highly viscous, swollen skins 5 of partially amorphous polymer, leaving the cores 3 of the original monofilaments 1 intact. The minimum effective thickness of the swollen skin needed to close the voids 4 is approximately 5% of the filament radius. Controlling the thickness of the skin above this value allows for creation of softened regions of the compound-filament, separating the highly oriented cores 3. For certain applications this can be a desirable property, in that the overall stiffness, particularly in bending and torsion, can be controlled. Crack propagation is also inhibited by these amorphous zones.

FIG. 2 schematically illustrates the processing equipment for production of the compound-filaments. Monofilaments 10 are fed from the bobbins 11, through the feed holes 12 into the sealed chamber 13. The chamber contains solvent 14 in equilibrium with the saturated solvent vapours 15 at the temperature $T_1$. Within the chamber 13 monofilaments 10 are arranged into the bundle 16. The bundle 16 is pulled through the conical orifice 17 into a second chamber 18. In the chamber 18 the solvent 14 is removed from the compound-filament 20 at temperature $T_2$ and under vacuum. Second chamber 18 is connected to a vacuum source via outlet 19. Compound-filament 20 is removed from the solvent by the action of the vacuum and pulled out from the chamber 18 through the seal 21 by the take-up rolls 22 rotating in different senses. Differently shaped (round, rectangular, plate, etc.) full cross sections of the compound-filament 20 can be produced by simply using an appropriate orifice 17. It is also possible to produce tubular sections as explained below.

Figure 3:
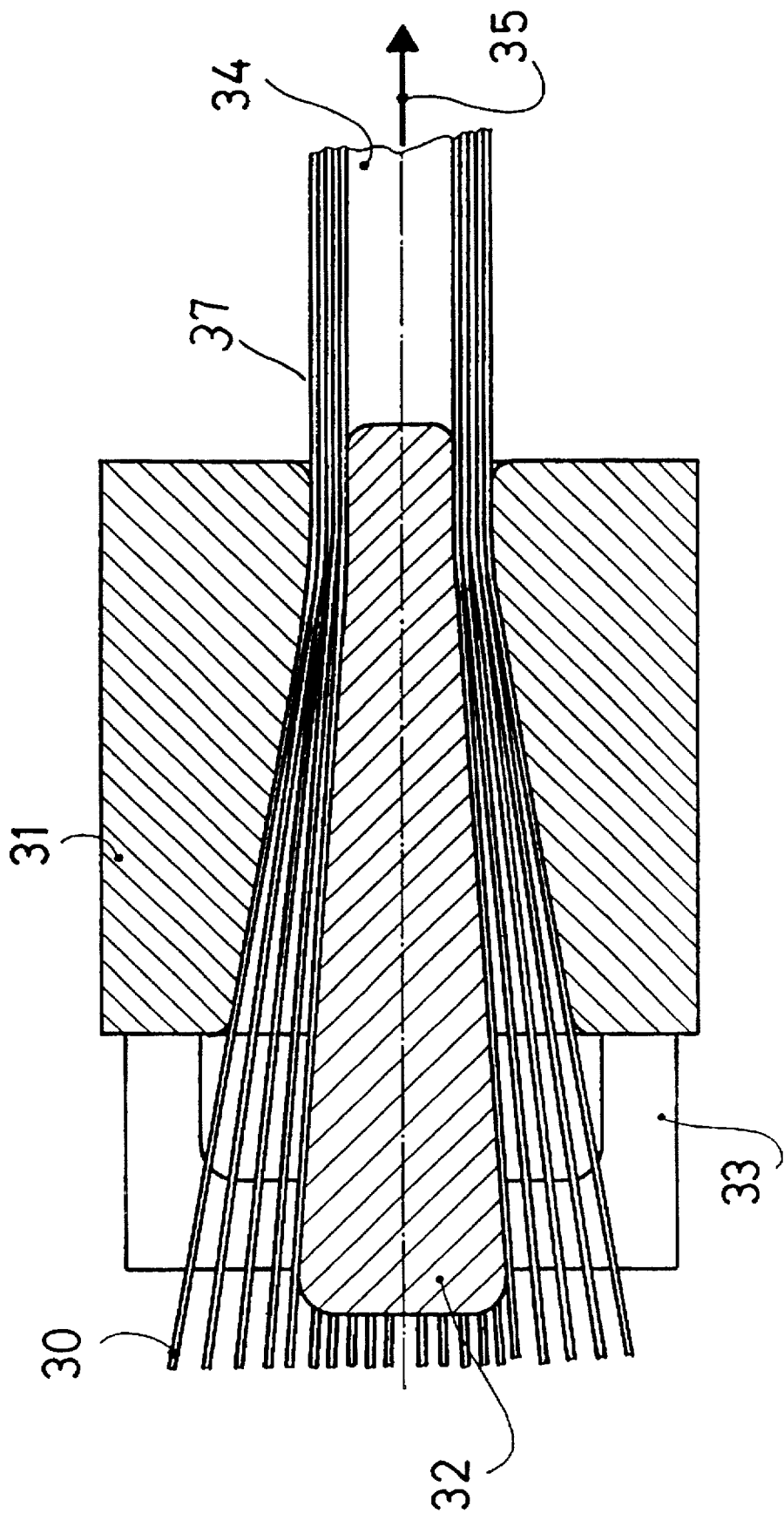
FIG. 3 is an enlarged sectional view of the annular orifice of the processing equipment for production of the compound-filaments of the implant materials according to the invention.

FIG. 3 shows for example an orifice for production of round tubular sections. Fibre bundle 30 is pulled into a conically shaped annular orifice 37 formed between the orifice body 31 and the conus 32. Conus 32 is held in place by a number of thin supports 33. Pulling the fibre bundle 30 as indicated by arrow 35 through the orifice 37 and maintaining tension on the bundle 30 past said orifice 37 while removing the solvent compounds individual monofilaments into a strong tube 34. Area of the smallest orifice opening is equal to or smaller than the total cross section of the fibres in the bundle 30. A possible use of such tubes 34 is for intramedullary nails in traumatology.

Figure 4A:
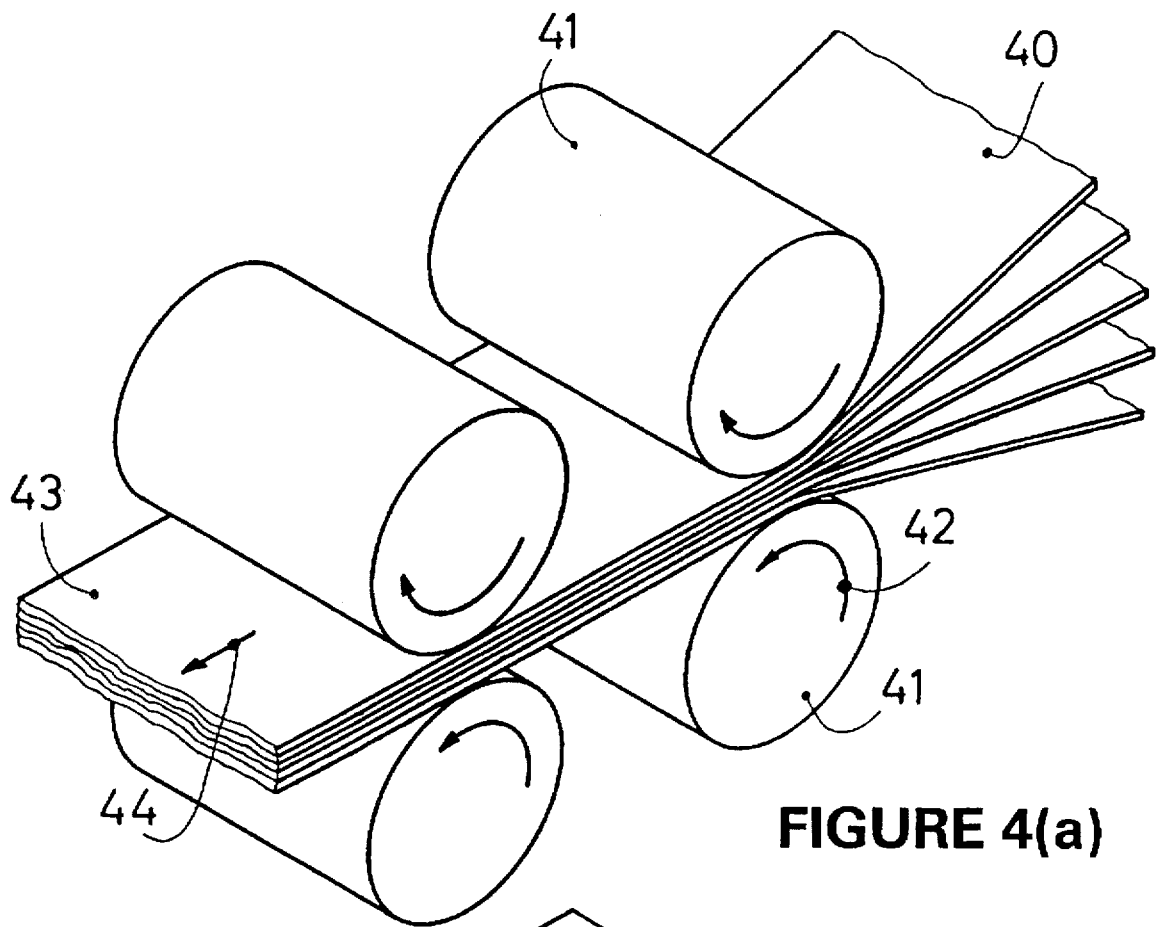
FIGS. 4(a) and 4(b) are perspective schematic views of the film-laminate compounding method according to the invention.

FIG. 4a shows the compounding process applied to film laminating.

Figure 4B:
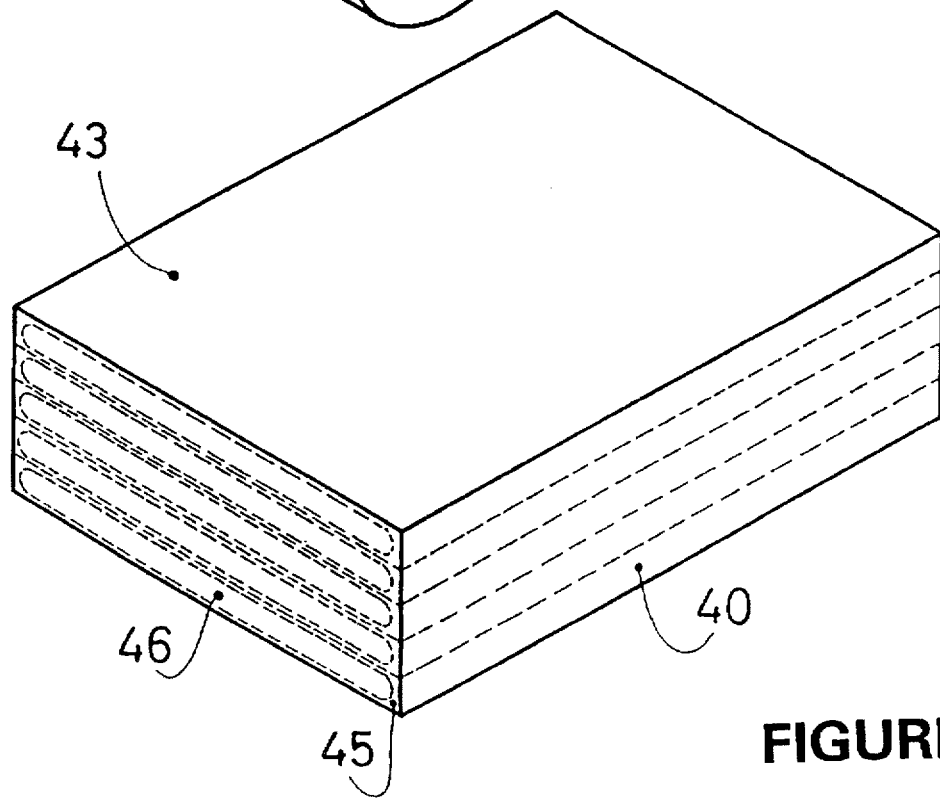

Film laminate 43 is produced by solvent swelling of the individual films 40 and pulling—in the direction of arrow 44—the sandwich of films 40 through an orifice formed by preferably a set of rollers 41 which can rotate either passively or actively in direction of arrow 42. By maintaining tension on the sandwich past said orifice formed by the set of rollers 41 and removing the solvent a strong film-laminate 43 is produced. As shown in FIG. 4b only a thin surface layer 45 of the single film 40 is swollen leaving the oriented high strength core 46 of the single film 40 intact.

Figure 5:
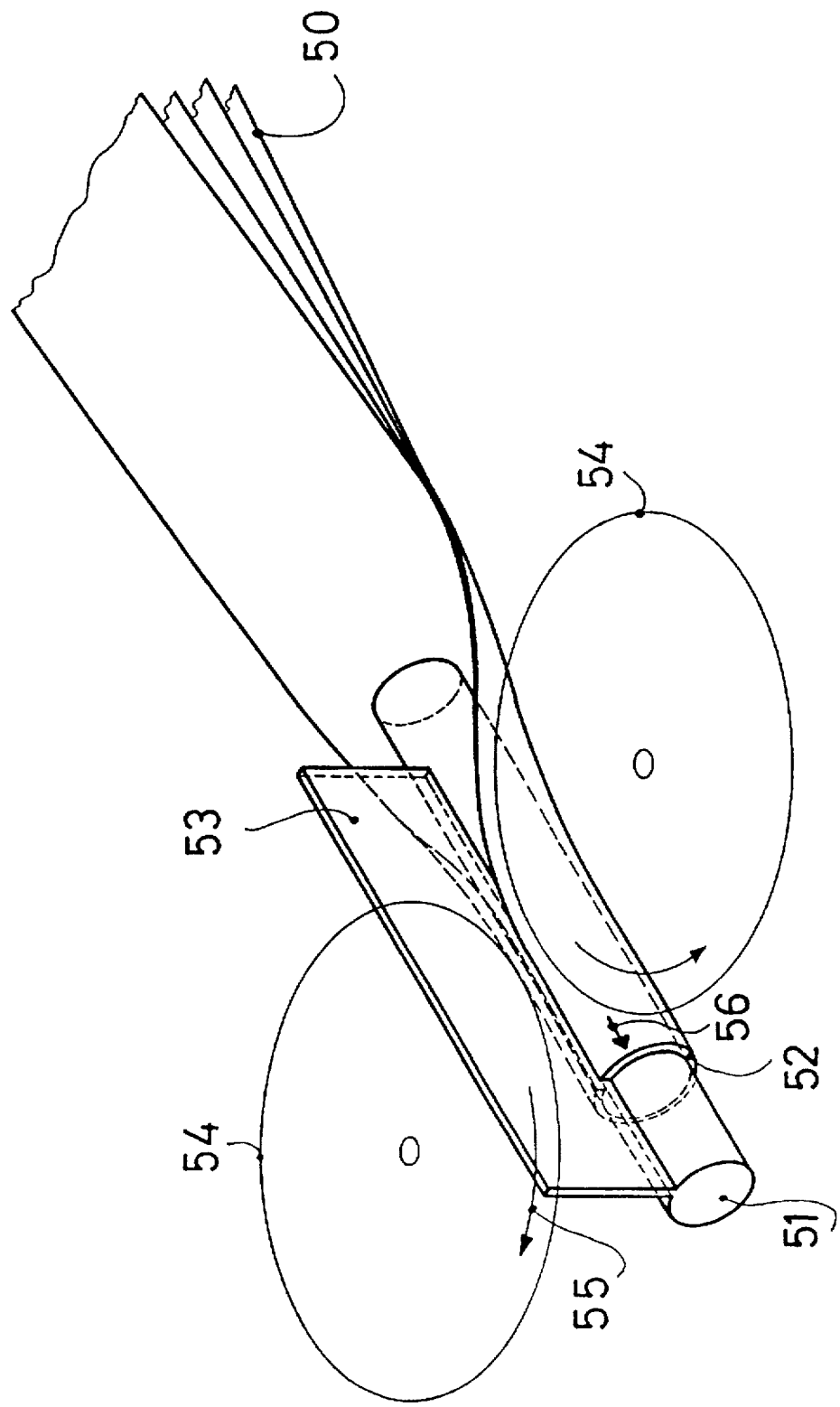
FIG. 5 is a perspective schematic view of the film-laminate compounding method according to the invention producing an open (slotted) tubular section.

FIG. 5 shows the film compounding process according to the invention used to form an open, i.e. slotted tube 52 suitable e.g. for the production of orthopaedic intramedullary nails. Highly oriented polymeric films 50 are surface swollen by means of a suitable solvent and wrapped around a core 51 having a radial blade 53 generating an open tubular section 52. Wrapping and compounding the films 50 together is achieved by a multitude of rollers 54 (of which only a set of two is shown in the figure) rotating in the direction of arrow 55. The core 51 preferably moves with the tube 52 in the direction of arrow 56. Continuous processing can be achieved by using a number of cores 51 which are fed into position contiguously one after the other. Cores 51 are removed from the tube 52 when the tube 52 is cut to length and are fed back in the continuous process.

Figure 6A:
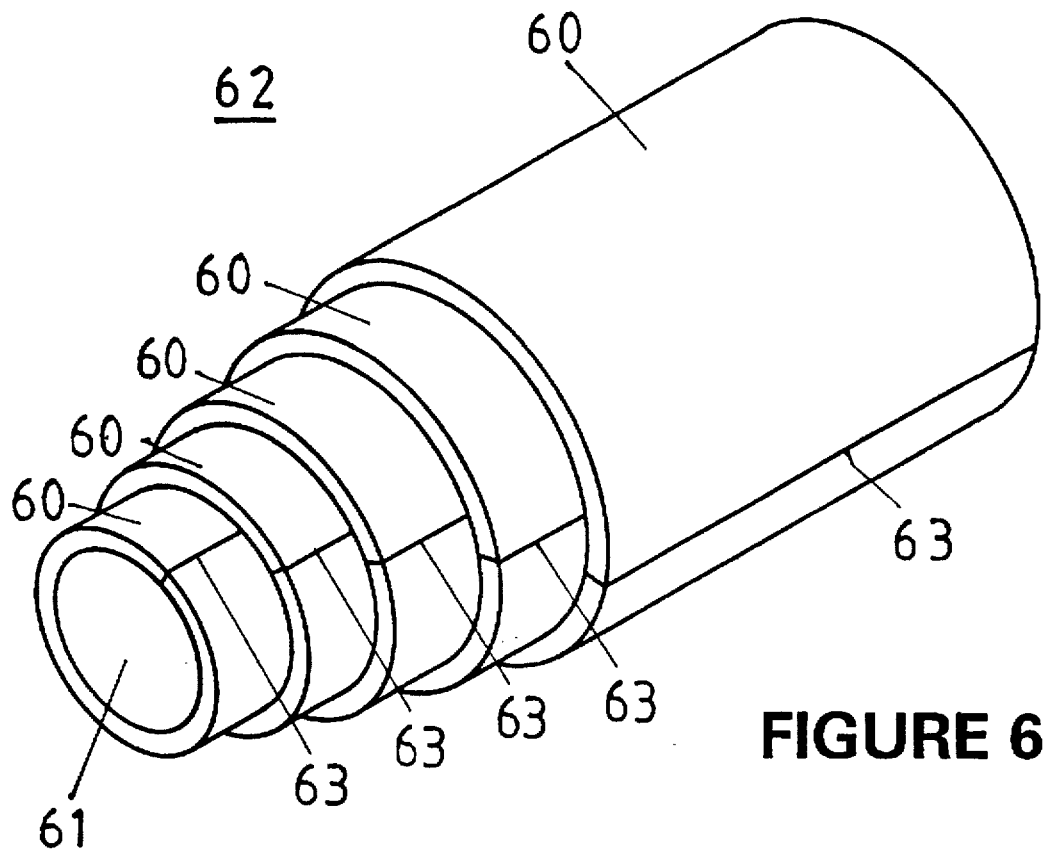
FIGS. 6(a) and 6(b) are perspective views of a film-laminated closed tubular section produced according to the invention.

As shown in FIG. 6 it is also possible to produce unslotted tubes by using a cylindrical core 61 without radial blade. The films 60 are wrapped around said core 61 in such a way that their abutting ends 63 are offset tangentially around the tube 62 as represented in FIG. 6a.

Figure 6B:
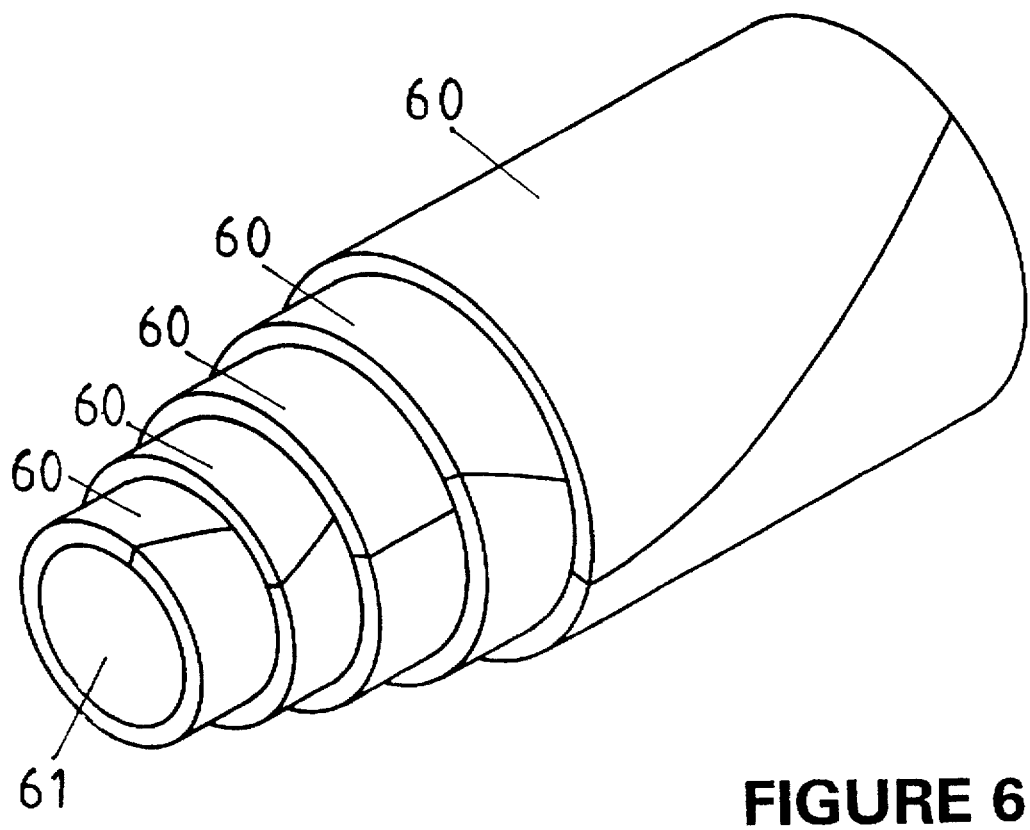

Further control of torsional stiffness can be achieved by spirally wound films 60 around the core 61 as shown in FIG. 6b.

A number of biocompatible chemical compounds are now listed which purposefully can be used as implant materials according to the invention.

Polyethylene

Ultra-high molecular weight polyethylene fibres are treated with vapours of boiling toluene according to the method described in this invention. Resulting high-modulus, high-strength compound-filament "rope" when cut to proper size, can be used as an intramedullary nail in osteosynthesis.

Polyethylene terephthalate

Polyethylene terephthalate fibres, monofilaments or films can be transformed into compound- filament and/or compound-film material according to the method described in this invention, by using vapours of boiling dimethylsulfoxide (DMSO).

Polycaproamide

Nylon 6 fibres can be transformed into compound-filament implant of the invention by passing the fibres through vapours of concentrated formic acid.

Polylactide

Hot-drawn polylactide fibres produced by melt-spinning or gel-extrusion as described by Gogolewski, Pennings, J Appl. Polym Sci 28, 1045–1061 (1983) can be processed into compound-filament implants according to the invention by using vapours of chlorinated or fluorinated hydrocarbon solvents, e.g. chloroform, methylene chloride or hexafluoropropanol.

We claim:

1. A method for producing high-strength, high-modulus, polymeric compound filament implant materials from oriented polymeric fibers, comprising the steps of:
    a) exposing the surface of a plurality of oriented polymeric monofilaments to a solvent able to swell said surface, and swelling said surface;
    b) forming an aligned bundle of said monofilaments with said solvent-swollen surface;
    c) pulling said bundle through an orifice, whereby the area of the orifice at the narrowest point is equal to or smaller than the total cross-sectional area of the monofilaments in the bundle; and
    d) maintaining tension on the bundle past said orifice and removing said solvent.

2. Method according to claim 1, wherein said orifice is annular.

3. The method according to claim 1, wherein step a) comprises feeding said oriented polymeric monofilaments into a first sealed chamber containing said solvent in equilibrium with vapors of said solvent, and step d) comprises pulling said bundle into a second sealed chamber connectable to a vacuum source via an outlet, applying a vacuum in said second chamber to remove said solvent and pulling said formed compound-filament out from said second chamber.

4. Method according to claim 1, wherein said polymeric fibres are made of ultra-high molecular weight polyethylene and said solvent is toluene.

5. The method of claim 1 wherein said polymeric fibers are made of polyethylene terephthalate and said solvent is dimethyl sulfoxide.

6. The method of claim 1 wherein the polymeric fibers are made of nylon 6 and the solvent is formic acid.

7. The method of claim 1 wherein the polymeric fibers are made of polylactide and the solvent is a chlorinated or fluorinated hydrocarbon.

8. The method of claim 1 wherein the polymeric fibers are made of polylactide and the solvent is selected from the group consisting of chloroform, methylene chloride and hexafluoropropanol.

* * * * *